(12) United States Patent
Prince et al.

(10) Patent No.: US 10,293,107 B2
(45) Date of Patent: May 21, 2019

(54) SELECTIVELY CONTROLLING FLUID FLOW THROUGH A FLUID PATHWAY

(75) Inventors: Stephen Michael Prince, La Jolla, CA (US); Walter John Bochenko, Encinitas, CA (US)

(73) Assignee: CRISI Medical Systems, Inc., Franklin Lakes, NJ (US)

( * ) Notice: Subject to any disclaimer, the term of this patent is extended or adjusted under 35 U.S.C. 154(b) by 926 days.

(21) Appl. No.: 13/529,876

(22) Filed: Jun. 21, 2012

(65) Prior Publication Data

US 2012/0325330 A1    Dec. 27, 2012

Related U.S. Application Data

(60) Provisional application No. 61/500,073, filed on Jun. 22, 2011.

(51) Int. Cl.
*A61M 5/168*    (2006.01)

(52) U.S. Cl.
CPC . *A61M 5/16881* (2013.01); *A61M 2205/3561* (2013.01); *A61M 2205/6009* (2013.01); *Y10T 137/0324* (2015.04); *Y10T 137/7722* (2015.04)

(58) Field of Classification Search
CPC ...... A61M 5/16881; A61M 2205/3561; A61M 2205/6009; A61M 2205/6018; A61M 2205/6063; A61M 2205/6072; A61M 2205/6081; Y10T 137/0324; Y10T 137/7722
See application file for complete search history.

(56) References Cited

U.S. PATENT DOCUMENTS

| | | | |
|---|---|---|---|
| 607,941 | A | 7/1898 | Mayo |
| 614,703 | A | 11/1898 | Delory |
| 3,430,625 | A | 3/1969 | McLeod, Jr. |
| 4,003,252 | A | 1/1977 | Dewath |
| 4,415,802 | A | 11/1983 | Long |
| 4,650,475 | A | 3/1987 | Smith et al. |
| 4,684,367 | A * | 8/1987 | Schaffer ............ A61M 5/1483 128/DIG. 12 |
| 4,853,521 | A | 8/1989 | Claeys et al. |

(Continued)

FOREIGN PATENT DOCUMENTS

| | | |
|---|---|---|
| CN | 101732778 A | 6/2010 |
| DE | 4137837 C1 | 10/1992 |

(Continued)

OTHER PUBLICATIONS

U.S. Appl. No. 12/614,276, filed Nov. 6, 2009, 2011-0112473.

(Continued)

*Primary Examiner* — Kami A Bosworth
(74) *Attorney, Agent, or Firm* — The Webb Law Firm

(57) ABSTRACT

Systems and methods for controlling fluid delivery via a manually administrable medication container to a patient through a fluid delivery pathway are provided. The systems and methods described herein incorporate rules-based clinical decision support logic to drive a flow control valve within a flow pathway to determine whether the IV fluid connected to the input port is consistent with medical orders, accepted delivery protocols, and/or specific patient and patient histories. Related apparatus, systems, methods and articles are also described.

46 Claims, 5 Drawing Sheets

(56) References Cited

U.S. PATENT DOCUMENTS

| | | |
|---|---|---|
| 4,857,713 A | 8/1989 | Brown |
| 4,921,277 A | 5/1990 | McDonough |
| 4,978,335 A | 12/1990 | Arthur, III |
| 5,011,032 A | 4/1991 | Rollman |
| 5,040,422 A | 8/1991 | Frankenberger et al. |
| 5,062,774 A * | 11/1991 | Kramer ............... A61J 3/002 128/DIG. 12 |
| 5,078,683 A | 1/1992 | Sancoff et al. |
| 5,179,862 A | 1/1993 | Lynnworth |
| 5,247,826 A | 9/1993 | Frola et al. |
| 5,279,576 A | 1/1994 | Loo et al. |
| 5,317,506 A | 5/1994 | Coutre et al. |
| 5,338,157 A | 8/1994 | Blomquist |
| 5,383,858 A | 1/1995 | Reilly et al. |
| 5,429,602 A | 7/1995 | Hauser |
| 5,463,906 A | 11/1995 | Spani et al. |
| 5,531,697 A | 7/1996 | Olsen et al. |
| 5,531,698 A | 7/1996 | Olsen |
| 5,569,212 A | 10/1996 | Brown |
| 5,611,784 A | 3/1997 | Barresi et al. |
| 5,612,524 A | 3/1997 | Sant'Anselmo et al. |
| 5,628,309 A | 5/1997 | Brown |
| 5,651,775 A | 7/1997 | Walker et al. |
| 5,692,640 A | 12/1997 | Caulfield et al. |
| 5,713,856 A | 2/1998 | Eggers et al. |
| 5,720,733 A | 2/1998 | Brown |
| 5,740,428 A | 4/1998 | Mortimore et al. |
| 5,781,442 A | 7/1998 | Engleson et al. |
| 5,782,814 A | 7/1998 | Brown et al. |
| 5,792,117 A | 8/1998 | Brown |
| 5,845,264 A | 12/1998 | Nellhaus |
| 5,873,731 A | 2/1999 | Prendergast |
| 5,882,338 A | 3/1999 | Gray |
| 5,920,263 A | 7/1999 | Huttenhoff et al. |
| 5,925,014 A | 7/1999 | Teeple, Jr. |
| 5,941,846 A | 8/1999 | Duffy et al. |
| 5,984,901 A | 11/1999 | Sudo et al. |
| 6,019,745 A | 2/2000 | Gray |
| 6,039,251 A | 3/2000 | Holowko et al. |
| 6,106,498 A | 8/2000 | Friedli et al. |
| 6,123,686 A | 9/2000 | Olsen et al. |
| 6,192,945 B1 | 2/2001 | Ford et al. |
| D438,634 S | 3/2001 | Merry |
| 6,249,299 B1 | 6/2001 | Tainer |
| 6,256,037 B1 | 7/2001 | Callahan |
| 6,270,455 B1 | 8/2001 | Brown |
| 6,277,099 B1 | 8/2001 | Strowe et al. |
| 6,338,200 B1 | 1/2002 | Baxa et al. |
| 6,341,174 B1 | 1/2002 | Callahan et al. |
| 6,342,889 B1 | 1/2002 | Callahan |
| 6,381,029 B1 | 4/2002 | Tipirneni |
| 6,422,094 B1 | 7/2002 | Ganshorn |
| 6,464,667 B1 | 10/2002 | Kamen et al. |
| 6,468,424 B1 | 10/2002 | Donig et al. |
| 6,471,089 B2 | 10/2002 | Liff et al. |
| 6,482,185 B1 | 11/2002 | Hartmann |
| 6,497,680 B1 | 12/2002 | Holst et al. |
| 6,519,569 B1 * | 2/2003 | White ............... A61M 5/142 604/151 |
| 6,579,231 B1 | 6/2003 | Phipps |
| RE38,189 E | 7/2003 | Walker et al. |
| 6,626,355 B2 | 9/2003 | Sasse et al. |
| 6,626,862 B1 | 9/2003 | Duchon et al. |
| D481,121 S | 10/2003 | Evans |
| 6,641,562 B1 | 11/2003 | Peterson |
| 6,644,130 B2 | 11/2003 | Imai et al. |
| 6,671,563 B1 | 12/2003 | Engleson et al. |
| D485,356 S | 1/2004 | Evans |
| 6,675,660 B1 | 1/2004 | Mosier et al. |
| 6,685,227 B2 | 2/2004 | Merry et al. |
| 6,685,678 B2 | 2/2004 | Evans et al. |
| 6,697,067 B1 | 2/2004 | Callahan et al. |
| 6,731,989 B2 | 5/2004 | Engleson et al. |
| 6,733,495 B1 | 5/2004 | Bek et al. |
| 6,742,992 B2 | 6/2004 | Davis |
| 6,790,198 B1 | 9/2004 | White et al. |
| 6,798,533 B2 | 9/2004 | Tipirneni |
| 6,825,864 B2 | 11/2004 | Botten et al. |
| 6,851,615 B2 | 2/2005 | Jones |
| 6,854,338 B2 | 2/2005 | Khuri-Yakub et al. |
| 6,915,170 B2 | 7/2005 | Engleson et al. |
| 6,960,192 B1 | 11/2005 | Flaherty et al. |
| 6,985,870 B2 | 1/2006 | Martucci et al. |
| 6,993,402 B2 | 1/2006 | Klass et al. |
| 7,000,485 B2 | 2/2006 | Ao et al. |
| 7,017,623 B2 | 3/2006 | Tribble et al. |
| 7,061,831 B2 | 6/2006 | De La Huerga |
| 7,074,205 B1 | 7/2006 | Duffy et al. |
| 7,074,209 B2 | 7/2006 | Evans et al. |
| 7,096,072 B2 | 8/2006 | Engleson et al. |
| 7,103,419 B2 | 9/2006 | Engleson et al. |
| 7,106,479 B2 | 9/2006 | Roy et al. |
| 7,107,106 B2 | 9/2006 | Engleson et al. |
| 7,115,113 B2 | 10/2006 | Evans et al. |
| 7,116,343 B2 | 10/2006 | Botten et al. |
| 7,117,041 B2 | 10/2006 | Engleson et al. |
| 7,161,488 B2 | 1/2007 | Frasch |
| 7,171,277 B2 | 1/2007 | Engleson et al. |
| 7,175,081 B2 | 2/2007 | Andreasson et al. |
| 7,180,624 B2 | 2/2007 | Tipirneni |
| 7,182,256 B2 | 2/2007 | Andreasson et al. |
| 7,225,683 B2 | 6/2007 | Harnett et al. |
| 7,236,936 B2 | 6/2007 | White et al. |
| 7,237,199 B1 | 6/2007 | Menhardt et al. |
| 7,264,323 B2 | 9/2007 | Tainer et al. |
| 7,299,981 B2 | 11/2007 | Hickle et al. |
| 7,319,540 B2 | 1/2008 | Tipirneni |
| 7,347,841 B2 | 3/2008 | Elhadad et al. |
| 7,358,505 B2 | 4/2008 | Woodworth et al. |
| 7,360,448 B2 | 4/2008 | Maginnis et al. |
| 7,364,067 B2 | 4/2008 | Steusloff et al. |
| 7,370,797 B1 | 5/2008 | Sullivan et al. |
| 7,375,737 B2 | 5/2008 | Botten et al. |
| 7,384,410 B2 | 6/2008 | Eggers et al. |
| 7,442,181 B2 | 10/2008 | Schubert et al. |
| 7,469,598 B2 | 12/2008 | Shkarlet et al. |
| 7,469,599 B2 | 12/2008 | Froehlich et al. |
| 7,470,266 B2 | 12/2008 | Massengale et al. |
| 7,483,756 B2 | 1/2009 | Engleson et al. |
| D588,200 S | 3/2009 | Langan et al. |
| 7,534,239 B1 | 5/2009 | Schneider et al. |
| D593,613 S | 6/2009 | Langan et al. |
| D595,361 S | 6/2009 | Langan et al. |
| 7,559,483 B2 | 7/2009 | Hickle et al. |
| 7,564,579 B2 | 7/2009 | Tipirneni |
| D597,608 S | 8/2009 | Langan et al. |
| D602,534 S | 10/2009 | Langan et al. |
| 7,614,545 B2 | 11/2009 | Christoffersen et al. |
| 7,617,739 B1 | 11/2009 | Dam |
| D605,228 S | 12/2009 | Langan et al. |
| D605,229 S | 12/2009 | Langan et al. |
| D605,230 S | 12/2009 | Langan et al. |
| 7,645,258 B2 | 1/2010 | White et al. |
| 7,673,527 B2 | 3/2010 | Ehring et al. |
| 7,694,565 B2 | 4/2010 | Koerdt et al. |
| 7,703,336 B2 | 4/2010 | Genosar |
| 7,704,231 B2 | 4/2010 | Pongpairochana et al. |
| 7,722,083 B2 | 5/2010 | McCarthy et al. |
| 7,727,196 B2 | 6/2010 | Neer |
| 7,753,880 B2 | 7/2010 | Malackowski |
| 7,753,891 B2 | 7/2010 | Tennican et al. |
| 7,756,724 B2 | 7/2010 | Gropper et al. |
| 7,763,006 B2 | 7/2010 | Tennican |
| D621,879 S | 8/2010 | Langan et al. |
| D621,880 S | 8/2010 | Langan et al. |
| 7,771,385 B2 | 8/2010 | Eggers et al. |
| D624,595 S | 9/2010 | Langan et al. |
| D624,596 S | 9/2010 | Langan et al. |
| 7,799,010 B2 | 9/2010 | Tennican |
| 7,813,939 B2 | 10/2010 | Clements et al. |
| 7,815,123 B2 | 10/2010 | Conner et al. |
| 7,815,605 B2 | 10/2010 | Souter |
| 7,819,838 B2 | 10/2010 | Ziegler et al. |
| 7,822,096 B2 | 10/2010 | Kuksenkov |

(56) References Cited

U.S. PATENT DOCUMENTS

| | | |
|---|---|---|
| 7,834,816 B2 | 11/2010 | Marino et al. |
| 7,859,473 B2 | 12/2010 | Gibson |
| D633,151 S | 2/2011 | Langan et al. |
| 7,887,513 B2 | 2/2011 | Nemoto et al. |
| D634,367 S | 3/2011 | Langan et al. |
| D634,368 S | 3/2011 | Langan et al. |
| D634,369 S | 3/2011 | Langan et al. |
| 7,905,861 B2 | 3/2011 | Rhinehart et al. |
| 7,918,830 B2 | 4/2011 | Langan et al. |
| 7,922,073 B2 | 4/2011 | de la Huerga |
| 7,927,313 B2 | 4/2011 | Stewart et al. |
| 7,933,780 B2 | 4/2011 | De La Huerga |
| 7,941,949 B2 | 5/2011 | Cloninger |
| D639,861 S | 6/2011 | Langan et al. |
| D639,862 S | 6/2011 | Langan et al. |
| D639,863 S | 6/2011 | Langan et al. |
| 7,967,778 B2 | 6/2011 | Nemoto et al. |
| D641,421 S | 7/2011 | Langan et al. |
| D641,422 S | 7/2011 | Langan et al. |
| 7,976,508 B2 | 7/2011 | Hoag |
| D643,468 S | 8/2011 | Langan et al. |
| D643,469 S | 8/2011 | Langan et al. |
| D643,470 S | 8/2011 | Langan et al. |
| D643,471 S | 8/2011 | Langan et al. |
| D643,472 S | 8/2011 | Langan et al. |
| 7,991,627 B2 | 8/2011 | Hutchinson et al. |
| D645,094 S | 9/2011 | Langan et al. |
| 8,031,347 B2 | 10/2011 | Edwards et al. |
| 8,035,517 B2 | 10/2011 | Gibson |
| D649,196 S | 11/2011 | Langan et al. |
| 8,059,297 B2 | 11/2011 | Tipirneni |
| 8,063,925 B2 | 11/2011 | Tainer et al. |
| 8,065,924 B2 | 11/2011 | Ziegler et al. |
| 8,069,060 B2 | 11/2011 | Tipirneni |
| 8,111,159 B2 | 2/2012 | Andreasson et al. |
| 8,133,178 B2 | 3/2012 | Brauker et al. |
| 8,140,349 B2 | 3/2012 | Hanson et al. |
| 8,151,835 B2 | 4/2012 | Khan et al. |
| 8,235,938 B2 | 8/2012 | Eggers et al. |
| 8,240,550 B2 | 8/2012 | Steusloff et al. |
| 8,303,547 B2 | 11/2012 | Brown |
| 8,328,082 B1 | 12/2012 | Bochenko et al. |
| 8,355,753 B2 | 1/2013 | Bochenko et al. |
| 8,385,972 B2 | 2/2013 | Bochenko et al. |
| 8,394,053 B2 | 3/2013 | Bochenko et al. |
| 8,480,834 B2 | 7/2013 | Rice et al. |
| 8,505,809 B2 | 8/2013 | Steusloff et al. |
| 8,606,596 B1 | 12/2013 | Bochenko et al. |
| 8,636,202 B2 | 1/2014 | Keefe et al. |
| 8,639,521 B2 | 1/2014 | Eggers et al. |
| 8,639,525 B2 | 1/2014 | Levine et al. |
| 8,645,154 B2 | 2/2014 | Eggers et al. |
| 8,702,674 B2 | 4/2014 | Bochenko |
| 8,752,088 B1 | 6/2014 | Harvey et al. |
| 2001/0020148 A1 | 9/2001 | Sasse et al. |
| 2001/0049608 A1 | 12/2001 | Hochman |
| 2001/0056258 A1 | 12/2001 | Evans |
| 2002/0040208 A1 | 4/2002 | Flaherty et al. |
| 2002/0077852 A1 | 6/2002 | Ford et al. |
| 2002/0088131 A1 | 7/2002 | Baxa et al. |
| 2002/0098598 A1 | 7/2002 | Coffen et al. |
| 2002/0099334 A1 | 7/2002 | Hanson et al. |
| 2002/0177811 A1 | 11/2002 | Reilly et al. |
| 2002/0188259 A1 | 12/2002 | Hickle et al. |
| 2003/0012701 A1 | 1/2003 | Sangha et al. |
| 2003/0052787 A1 | 3/2003 | Zerhusen et al. |
| 2003/0055685 A1 | 3/2003 | Cobb et al. |
| 2003/0065537 A1 | 4/2003 | Evans |
| 2003/0088238 A1 | 5/2003 | Poulsen et al. |
| 2003/0135388 A1 | 7/2003 | Martucci et al. |
| 2003/0139701 A1 | 7/2003 | White et al. |
| 2003/0139706 A1 | 7/2003 | Gray |
| 2003/0140929 A1 | 7/2003 | Wilkes et al. |
| 2003/0141981 A1 | 7/2003 | Bui et al. |
| 2003/0160698 A1 | 8/2003 | Andreasson et al. |
| 2003/0164401 A1 | 9/2003 | Andreasson et al. |
| 2003/0174326 A1 | 9/2003 | Rzasa et al. |
| 2004/0051368 A1 | 3/2004 | Caputo et al. |
| 2004/0082918 A1 | 4/2004 | Evans et al. |
| 2004/0092885 A1 | 5/2004 | Duchon et al. |
| 2004/0103951 A1 | 6/2004 | Osborne et al. |
| 2004/0104271 A1 | 6/2004 | Martucci et al. |
| 2004/0105115 A1 | 6/2004 | Edwards et al. |
| 2004/0179051 A1 | 9/2004 | Tainer et al. |
| 2004/0179132 A1 | 9/2004 | Fujino et al. |
| 2004/0186437 A1 | 9/2004 | Frenette et al. |
| 2004/0193453 A1 | 9/2004 | Butterfield et al. |
| 2004/0204673 A1 | 10/2004 | Flaherty |
| 2004/0212834 A1 | 10/2004 | Edwards et al. |
| 2004/0238631 A1 | 12/2004 | Andreasson et al. |
| 2005/0055242 A1 | 3/2005 | Bello et al. |
| 2005/0059926 A1 | 3/2005 | Sage, Jr. et al. |
| 2005/0070978 A1 | 3/2005 | Bek et al. |
| 2005/0088306 A1 | 4/2005 | Andreasson et al. |
| 2005/0101905 A1 | 5/2005 | Merry |
| 2005/0106225 A1 | 5/2005 | Massengale et al. |
| 2005/0107923 A1 | 5/2005 | Vanderveen |
| 2005/0118048 A1 | 6/2005 | Traxinger |
| 2005/0151652 A1 | 7/2005 | Frasch |
| 2005/0151823 A1 | 7/2005 | Botten et al. |
| 2005/0154368 A1 | 7/2005 | Lim et al. |
| 2005/0165559 A1 | 7/2005 | Nelson |
| 2005/0182358 A1 | 8/2005 | Veit et al. |
| 2005/0189252 A1* | 9/2005 | Naylor .................. A61L 2/28 206/439 |
| 2005/0277873 A1 | 12/2005 | Stewart et al. |
| 2005/0277890 A1 | 12/2005 | Stewart et al. |
| 2006/0032918 A1 | 2/2006 | Andreasson et al. |
| 2006/0065713 A1 | 3/2006 | Kingery |
| 2006/0079767 A1 | 4/2006 | Gibbs et al. |
| 2006/0079843 A1 | 4/2006 | Brooks et al. |
| 2006/0102503 A1 | 5/2006 | Elhadad et al. |
| 2006/0116639 A1 | 6/2006 | Russell |
| 2006/0122577 A1 | 6/2006 | Poulsen et al. |
| 2006/0143051 A1 | 6/2006 | Eggers et al. |
| 2006/0144942 A1 | 7/2006 | Evans et al. |
| 2006/0178617 A1 | 8/2006 | Adams et al. |
| 2006/0190302 A1 | 8/2006 | Eggers et al. |
| 2006/0206356 A1 | 9/2006 | Vanderveen |
| 2006/0224125 A1 | 10/2006 | Simpson et al. |
| 2006/0226089 A1 | 10/2006 | Robinson et al. |
| 2006/0229551 A1 | 10/2006 | Martinez et al. |
| 2006/0253346 A1 | 11/2006 | Gomez |
| 2006/0258985 A1 | 11/2006 | Russell |
| 2006/0265186 A1 | 11/2006 | Holland et al. |
| 2006/0270997 A1 | 11/2006 | Lim et al. |
| 2006/0287887 A1 | 12/2006 | Hutchinson et al. |
| 2007/0008399 A1 | 1/2007 | Botten et al. |
| 2007/0043335 A1 | 2/2007 | Olsen et al. |
| 2007/0060874 A1 | 3/2007 | Nesbitt et al. |
| 2007/0100316 A1 | 5/2007 | Traxinger |
| 2007/0134044 A1 | 6/2007 | Colbrunn et al. |
| 2007/0135765 A1 | 6/2007 | Miller et al. |
| 2007/0136218 A1 | 6/2007 | Bauer et al. |
| 2007/0166198 A1 | 7/2007 | Sangha et al. |
| 2007/0167919 A1 | 7/2007 | Nemoto et al. |
| 2007/0179448 A1 | 8/2007 | Lim et al. |
| 2007/0186923 A1 | 8/2007 | Poutiatine et al. |
| 2007/0187475 A1 | 8/2007 | MacLeod |
| 2007/0191787 A1 | 8/2007 | Lim et al. |
| 2007/0255199 A1 | 11/2007 | Dewey |
| 2007/0279625 A1 | 12/2007 | Rzasa et al. |
| 2007/0280710 A1 | 12/2007 | Tainer et al. |
| 2007/0293830 A1 | 12/2007 | Martin |
| 2007/0299421 A1 | 12/2007 | Gibson |
| 2008/0045930 A1 | 2/2008 | Makin et al. |
| 2008/0051937 A1 | 2/2008 | Khan et al. |
| 2008/0061153 A1 | 3/2008 | Hickle et al. |
| 2008/0065016 A1 | 3/2008 | Peterson et al. |
| 2008/0071219 A1 | 3/2008 | Rhinehart et al. |
| 2008/0118141 A1 | 5/2008 | Sommer et al. |
| 2008/0125724 A1 | 5/2008 | Monroe |
| 2008/0191013 A1 | 8/2008 | Liberatore |
| 2008/0208042 A1 | 8/2008 | Ortenzi et al. |

(56) References Cited

U.S. PATENT DOCUMENTS

| | | | |
|---|---|---|---|
| 2008/0234630 A1 | 9/2008 | Iddan et al. | |
| 2008/0243054 A1 | 10/2008 | Mollstam et al. | |
| 2008/0243088 A1 | 10/2008 | Evans | |
| 2008/0255523 A1 | 10/2008 | Grinberg | |
| 2008/0287889 A1* | 11/2008 | Sharvit | A61B 5/117 604/251 |
| 2008/0294108 A1 | 11/2008 | Briones et al. | |
| 2008/0306439 A1 | 12/2008 | Nelson et al. | |
| 2009/0018494 A1 | 1/2009 | Nemoto et al. | |
| 2009/0030730 A1 | 1/2009 | Dullemen et al. | |
| 2009/0036846 A1 | 2/2009 | Dacquay et al. | |
| 2009/0043253 A1 | 2/2009 | Podaima | |
| 2009/0069714 A1 | 3/2009 | Eichmann et al. | |
| 2009/0069743 A1 | 3/2009 | Krishnamoorthy et al. | |
| 2009/0085768 A1 | 4/2009 | Patel et al. | |
| 2009/0112178 A1 | 4/2009 | Behzadi | |
| 2009/0112333 A1 | 4/2009 | Sahai | |
| 2009/0113996 A1* | 5/2009 | Wang | A61M 5/1413 73/54.43 |
| 2009/0126483 A1 | 5/2009 | Blendinger et al. | |
| 2009/0126866 A1 | 5/2009 | Stenner et al. | |
| 2009/0137956 A1 | 5/2009 | Souter | |
| 2009/0143673 A1 | 6/2009 | Drost et al. | |
| 2009/0149744 A1 | 6/2009 | Nemoto et al. | |
| 2009/0156931 A1 | 6/2009 | Nemoto et al. | |
| 2009/0156985 A1* | 6/2009 | Hottmann | A61F 9/00736 604/35 |
| 2009/0157008 A1 | 6/2009 | Vitral | |
| 2009/0159654 A1 | 6/2009 | Grimard | |
| 2009/0200185 A1 | 8/2009 | Follman et al. | |
| 2009/0209911 A1* | 8/2009 | Cabus | A61M 5/14244 604/140 |
| 2009/0259176 A1 | 10/2009 | Yairi | |
| 2009/0288497 A1 | 11/2009 | Ziegler et al. | |
| 2009/0294521 A1 | 12/2009 | de la Huerga | |
| 2009/0296540 A1 | 12/2009 | Gilbert et al. | |
| 2009/0306620 A1 | 12/2009 | Thilly et al. | |
| 2009/0312635 A1 | 12/2009 | Shimchuk et al. | |
| 2010/0022953 A1 | 1/2010 | Bochenko et al. | |
| 2010/0022987 A1 | 1/2010 | Bochenko et al. | |
| 2010/0036310 A1 | 2/2010 | Hillman | |
| 2010/0036313 A1 | 2/2010 | Shener et al. | |
| 2010/0065633 A1 | 3/2010 | Nelson et al. | |
| 2010/0065643 A1 | 3/2010 | Leyvraz et al. | |
| 2010/0076310 A1 | 3/2010 | Wenderow et al. | |
| 2010/0095782 A1 | 4/2010 | Ferencz et al. | |
| 2010/0114951 A1 | 5/2010 | Bauman et al. | |
| 2010/0145165 A1 | 6/2010 | Merry | |
| 2010/0152562 A1 | 6/2010 | Goodnow et al. | |
| 2010/0153136 A1 | 6/2010 | Whittacre et al. | |
| 2010/0164727 A1* | 7/2010 | Bazargan | A61M 5/14244 340/573.1 |
| 2010/0174266 A1 | 7/2010 | Estes | |
| 2010/0179417 A1 | 7/2010 | Russo | |
| 2010/0204659 A1 | 8/2010 | Bochenko et al. | |
| 2010/0262002 A1 | 10/2010 | Martz | |
| 2010/0280486 A1 | 11/2010 | Khair et al. | |
| 2010/0286599 A1 | 11/2010 | Ziegler et al. | |
| 2010/0305499 A1 | 12/2010 | Matsiev et al. | |
| 2011/0009800 A1 | 1/2011 | Dam et al. | |
| 2011/0009817 A1 | 1/2011 | Bennett et al. | |
| 2011/0028937 A1 | 2/2011 | Powers et al. | |
| 2011/0060198 A1 | 3/2011 | Bennett et al. | |
| 2011/0093279 A1 | 4/2011 | Levine et al. | |
| 2011/0111794 A1 | 5/2011 | Bochenko et al. | |
| 2011/0112473 A1 | 5/2011 | Bochenko et al. | |
| 2011/0112474 A1 | 5/2011 | Bochenko et al. | |
| 2011/0137288 A1 | 6/2011 | Tallarida et al. | |
| 2011/0152824 A1 | 6/2011 | DiPerna et al. | |
| 2011/0152825 A1 | 6/2011 | Marggi | |
| 2011/0152834 A1 | 6/2011 | Langan et al. | |
| 2011/0160655 A1 | 6/2011 | Hanson et al. | |
| 2011/0161112 A1 | 6/2011 | Keefe et al. | |
| 2011/0166511 A1 | 7/2011 | Sharvit et al. | |
| 2011/0176490 A1 | 7/2011 | Mehta et al. | |
| 2011/0185821 A1 | 8/2011 | Genosar | |
| 2011/0220713 A1 | 9/2011 | Cloninger | |
| 2011/0224649 A1 | 9/2011 | Duane et al. | |
| 2011/0259954 A1 | 10/2011 | Bartz et al. | |
| 2011/0264069 A1 | 10/2011 | Bochenko | |
| 2011/0295191 A1 | 12/2011 | Injev | |
| 2011/0313349 A1 | 12/2011 | Krulevitch et al. | |
| 2011/0315611 A1 | 12/2011 | Fulkerson et al. | |
| 2012/0004542 A1 | 1/2012 | Nemoto et al. | |
| 2012/0004602 A1 | 1/2012 | Hanson et al. | |
| 2012/0004637 A1 | 1/2012 | Krulevitch et al. | |
| 2012/0006127 A1 | 1/2012 | Nielsen | |
| 2012/0022458 A1 | 1/2012 | Oh et al. | |
| 2012/0035535 A1 | 2/2012 | Johnson et al. | |
| 2012/0037266 A1 | 2/2012 | Bochenko | |
| 2012/0041355 A1 | 2/2012 | Edman et al. | |
| 2012/0046295 A1 | 2/2012 | Charrier et al. | |
| 2012/0065617 A1 | 3/2012 | Matsiev et al. | |
| 2012/0073673 A1 | 3/2012 | Kameyama | |
| 2012/0222468 A1 | 9/2012 | Nelson et al. | |
| 2012/0226446 A1 | 9/2012 | Nelson et al. | |
| 2012/0226447 A1 | 9/2012 | Nelson et al. | |
| 2012/0287431 A1 | 11/2012 | Matsiev et al. | |
| 2012/0323208 A1 | 12/2012 | Bochenko et al. | |
| 2012/0325330 A1 | 12/2012 | Prince et al. | |
| 2013/0018356 A1 | 1/2013 | Prince et al. | |
| 2013/0105568 A1 | 5/2013 | Jablonski et al. | |
| 2013/0135388 A1 | 5/2013 | Samoto et al. | |
| 2013/0181046 A1 | 7/2013 | Fedorko et al. | |
| 2013/0204227 A1 | 8/2013 | Bochenko et al. | |
| 2013/0225945 A1 | 8/2013 | Prince et al. | |
| 2013/0226137 A1 | 8/2013 | Brown | |
| 2013/0327822 A1 | 12/2013 | Keefe et al. | |
| 2014/0039383 A1 | 2/2014 | Dobbles et al. | |
| 2014/0060729 A1 | 3/2014 | Srnka et al. | |
| 2014/0142975 A1 | 5/2014 | Keefe et al. | |
| 2015/0204705 A1 | 7/2015 | Forster et al. | |
| 2015/0211904 A1 | 7/2015 | Forster | |

FOREIGN PATENT DOCUMENTS

| | | |
|---|---|---|
| DE | 29617777 U1 | 12/1996 |
| EP | 1944709 A1 | 7/2008 |
| EP | 1980974 A2 | 10/2008 |
| EP | 2135630 A1 | 12/2009 |
| GB | 2183046 B | 5/1987 |
| GB | 2504288 A | 1/2014 |
| GB | 2504295 A | 1/2014 |
| GB | 2504297 A | 1/2014 |
| JP | 5317421 A | 12/1993 |
| JP | 2008517646 A | 5/2008 |
| JP | 201266004 A | 4/2012 |
| KR | 1020090025392 A | 3/2009 |
| WO | 03063932 A2 | 8/2003 |
| WO | 2009114115 A1 | 9/2009 |
| WO | 2010144482 A2 | 12/2010 |
| WO | 2011126485 A1 | 10/2011 |
| WO | 2012034084 A2 | 3/2012 |
| WO | 2012126744 A1 | 9/2012 |
| WO | 2013096713 A2 | 6/2013 |
| WO | 2014016311 A1 | 1/2014 |
| WO | 2014016315 A1 | 1/2014 |
| WO | 2014016316 A1 | 1/2014 |

OTHER PUBLICATIONS

U.S. Appl. No. 12/765,707, filed Apr. 22, 2010, 2011-0111794.
U.S. Appl. No. 12/768,509, filed Apr. 27, 2010, 2011-0264069.
U.S. Appl. No. 12/938,300, filed Nov. 2, 2010, 2011-0112474.
U.S. Appl. No. 13/149,782, filed May 31, 2011.
U.S. Appl. No. 13/170,073, filed Jun. 27, 2011.
U.S. Appl. No. 13/282,255, filed Oct. 26, 2011, 2012-0037266.
U.S. Appl. No. 13/524,736, filed Jun. 15, 2012.
U.S. Appl. No. 13/549,278, filed Jul. 13, 2012.
U.S. Appl. No. 61/551,916, filed Oct. 26, 2011.
Google Scholar Search [Jul. 21, 2014].

(56) References Cited

OTHER PUBLICATIONS

U.S. Appl. No. 13/524,736, filed Jun. 15, 2012, 2012-0323208.
U.S. Appl. No. 13/549,278, filed Jul. 13, 2012, 2013-0018356.
U.S. Appl. No. 13/689,729, filed Nov. 29, 2012, 2014-0066880.
U.S. Appl. No. 13/777,831, filed Feb. 26, 2013, 2013-0225945.
U.S. Appl. No. 13/777,964, filed Feb. 26, 2013, 2013-0204227.
U.S. Appl. No. 13/802,231, filed Mar. 13, 2013, 2014-0276213.
U.S. Appl. No. 13/671,752, filed Nov. 8, 2012.
International Search Report dated Aug. 2, 2011 for corresponding PCT Application No. PCT/US2010/055322.

* cited by examiner

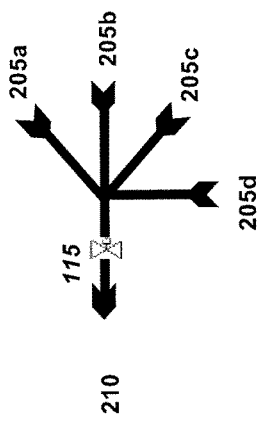
FIG. 2E
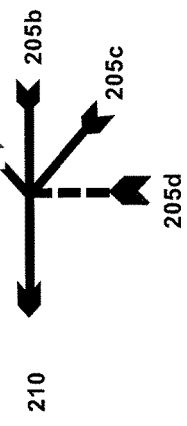
FIG. 2F
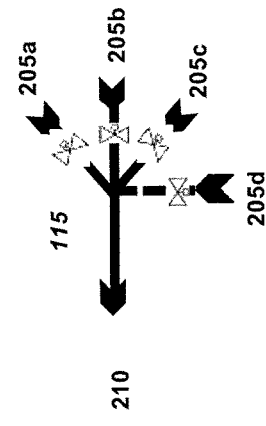
FIG. 2G
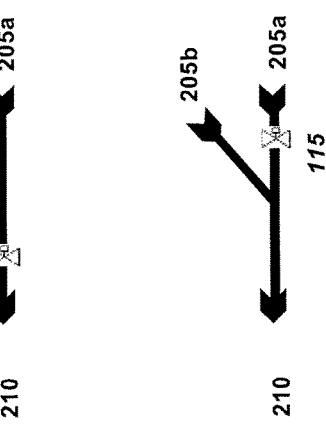
FIG. 2A
FIG. 2B
FIG. 2C
FIG. 2D

SELECTIVELY CONTROLLING FLUID FLOW THROUGH A FLUID PATHWAY

RELATED APPLICATION

This application claims priority to U.S. Pat. App. Ser. No. 61/500,073, filed on Jun. 22, 2011 the contents of which are hereby fully incorporated by reference.

FIELD

The subject matter described herein relates to systems and methods for controlling fluid flow to a patient through a fluid pathway.

BACKGROUND

There are a number of patient clinical settings including in-hospital, outpatient, in-home care and emergency medical services (EMS) that require fluid administration to a patient. Standard clinical best practice is to label fluids intended to be delivered to patients to reduce the potential for errors. However, mistakes in compatibility of fluids with a particular patient, incorrect dose measurements, inappropriate sequence of medications, incorrect transfer of labeling information and other factors are a major obstacle to overcome in patient care.

SUMMARY

In one aspect, an apparatus includes a fluid inlet, a fluid outlet, a fluid flow stop, an identification sensor, and a flow state controller. The fluid inlet is configured to couple to an outlet of a manually administrable fluid source having fluid source information encoded thereon. The fluid outlet is configured to deliver fluid from the manually administrable fluid source to a fluid line leading to a patient. The fluid flow stop is disposed between the fluid inlet and the fluid outlet that prevents fluid flow in a first state and permits fluid flow in a second state. The identification sensor to detect the fluid source information when the manually administrable fluid source is being coupled or is coupled to the fluid inlet. The flow state controller selectively causes the fluid flow stop to transition between the first state and the second state based on the fluid source information detected by the identification sensor.

The flow state controller can use a plurality of rules to determine whether to transition the current state of the fluid flow stop to the other state. Some or all of the rules can be obtained from a remote data source polled by the flow state controller. A rules engine (i.e., software and/or hardware for applying the rules, etc.) can take into account the fluid source information, flow control input data, and one or more attributes of the patient and their history, clinical circumstances, environmental factors, clinical best practices and the like. The rules engine can be configurable and programmable according to one or more of user-inputted specifications (via for example, an interface on the apparatus or via a remote computing system/interface, etc.), patient specific data, and/or medication specific data.

A fluid composition sensor can be additionally incorporated to characterize a composition of the fluid when the manually administrable fluid source is coupled to the fluid inlet. In some cases, the fluid composition sensor can be used in place of the identification sensor while in other implementations it is used in combination with the identification sensor. In either arrangement, the flow state controller can further selectively cause the fluid flow stop to transition between the first state and the second state based on the fluid composition detected by the fluid composition sensor.

The flow state controller can transmit data characterizing the fluid source information detected by the identification sensor to a remote rules engine that sends a signal indicating whether to change a current state of the fluid flow stop. The fluid source information can be indicative of a characteristic of the fluid (e.g., medication, etc.) contained therein and can include one or more of an NDC code (National Drug Code), a segment of the NDC code identifying the drug product, a segment of the NDC code identifying the drug package, a unique identifier code, a human readable alphanumeric string, a machine readable code, a name of the medication, a manufacturer of the medication, a re-packager of the medication, a distributor of the medication, a strength of the medication, a dosage form of the medication, dose instructions for the medication, administration instructions for a specific patient, medication formulation, medication package form, medication package size, medication contained volume, medication package serial number, medication lot number, and medication expiration date, fluid type, and blood type. The fluid source information can include a code or identifier used to reference a secondary data set that is characteristic of the fluid contained therein (i.e., a reference to a lookup table, a database object, a URL, etc.). The apparatus can include memory that stores the secondary data set locally and/or a remote data store can be coupled to the flow state controller that stores the secondary data set. The remote data store can form part of a medical device or medical information system.

The transition between states can be automatically initiated and executed by the flow state controller without user intervention. The transition between states can be automatically initiated and executed by the flow state controller as a result of coupling the fluid source outlet to the fluid inlet.

An interface can be included to provide audio and/or visual feedback to a user characterizing one or more of the fluid source information, volume of fluid administration, rules engine information, and/or rules engine output. The interface can provide an indication to the user when the fluid flow stop is in the first state, an indication to the user of one or more rules used by a rules engine causing a fluid flow stop state transition, and/or an indication to the user without a fluid flow stop state transition. The interface can be adjacent to the fluid inlet and/or it can be remote from the fluid inlet (e.g., a display monitor wirelessly coupled to the flow state controller, etc).

The interface can display medication administration information associated with the fluid. Such medication administration information can be stored on local memory. A communications module can be included to transmit and/or receive the medication administration information to or from a remote data source. The interface can be adjacent to or remote from the fluid inlet.

A manual override element, which when activated by a user, can cause the flow state controller to cause the fluid flow stop to transition from the first state to the second state.

A communications module can be included to transmit and/or receive data to or from a remote data source characterizing one or more of the flow control input data, fluid source, the rules or a portion of the rules, and/or the patient.

In some implementations, there can be a plurality of fluid inlets that are each configured to couple to an outlet of one of a plurality of manually administrable fluid sources each having fluid source information thereon. In these arrangements, there can be a plurality of fluid flow stops that are each coupled to the flow state controller to selectively prevent fluid flow in at least one of the plurality of fluid inlets.

The fluid flow stop can be maintained in the first state until it is determined, by using the fluid source information, to transition the fluid flow stop to the second state. The fluid flow stop can be maintained in the second state until it is determined, by using the fluid source information, to transition the fluid flow stop to the first state. The flow state controller can receive data characterizing the patient that is used, in combination with the fluid flow source information, to determine whether to transition the current state of the fluid flow stop. The data characterizing the patient can include, for example, a medication order that is used to confirm whether the fluid in the fluid source matches one or more parameters specified by the at least one medication order. The data characterizing the patient can include a patient identifier that the flow state controller uses to poll at least one remote data store using the patient identifier to obtain reference information for the flow state controller to determine whether to transition the current state of the fluid flow stop.

A fluid flow sensor can be utilized that measures how much fluid has been delivered from the fluid source into the fluid inlet. The flow state controller can cause the fluid flow stop to transition from the second state to the first state when a pre-determined volume has been delivered as measured by the fluid flow sensor. An interface can provide audio and/or visual feedback indicating how much fluid has been delivered as measured by the fluid flow sensor. The flow state controller can cause the fluid flow stop to transition from the second state to the first state when a first pre-determined volume has been delivered as measured by the fluid flow sensor, and after a pre-determined span of time, can cause the fluid flow stop to transition from the first state to the second state. The rules can utilize flow control input data information such as fluid information, patient-specific information, medical order information, clinical guideline information, contraindications, environmental factor information including time, flow control valve status, and historical information.

The identification sensor can detect the fluid source information using one or more technologies selected from a group consisting of: optical, magnetic, mechanical, conductive, switchable, infrared, switchable RFID and proximity sensors. In some cases, the identification sensor includes an optical element which detects an identifier encoded on a tip/outlet of the manually injectable medication container.

A housing can envelope at least a portion of each of the fluid inlet, the fluid outlet, the fluid flow stop, the identification sensor, and the flow state controller. Such a housing can have a compact form/shape and size that allows a user to hold the housing in a first hand while activating the manually injectable medication container in a second hand. The housing can also include a self-contained power source within the housing powering the fluid flow stop, the identification sensor, and the flow state controller and the fluid line can be an intravenous (IV) fluid line. The compact housing can, for example, be suspected from the IV fluid line.

The housing can be subdivided into reusable sub-housing and a disposable sub-housing. The reusable sub-housing can be operatively coupled to the disposable sub-housing with the reusable sub-housing being intended for use by a plurality of patients and the disposable sub-housing being intended for use by a single patient. The disposable sub-housing can contain at least the fluid inlet, fluid outlet, flow channel, and fluid flow stop. The disposable sub-housing can be part of a kit including a sterile pouch enveloping the disposable sub-housing. The disposable sub-housing can include memory for storing data that can include flow stop configuration information, flow sensor calibration information and/or a serial number or a unique identification number.

In an interrelated aspect, fluid source information of a manually administrable fluid source is detected by an identification sensor of a fluid delivery device, Thereafter, it is determined, using the detected fluid source information, whether to transition the current state of the fluid flow stop to the other state. A flow state controller of the fluid delivery device then causes a fluid flow stop to transition to the other state (e.g., open or closed) if it is determined that the fluid flow stop should transition to the other state. Otherwise, the current state of the fluid flow stop is maintained if it is not determined that the fluid flow stop should transition to the other state.

Computer program products are also described that comprise non-transitory computer readable media storing instructions, which when executed by at least one data processor of one or more computing systems, causes the at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. For example, the rules engine can be software-based or a combination of software-hardware based.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings:

FIGS. 2A-2G are diagrams illustrating alternative configurations of a fluid delivery pathway having a flow control valve;

Like reference symbols in the various drawings indicate like or similar elements.

DETAILED DESCRIPTION

Described herein are systems and methods for controlling fluid delivery to a patient through a fluid delivery pathway. The systems and methods described herein incorporate a rules-based clinical decision support logic to drive a flow control valve within a flow pathway to determine whether the IV fluid connected to the input port is appropriate for delivery to a specific patient (consistent with medical orders, accepted delivery protocols, and/or specific patient and patient histories, etc.).

It is standard practice to query patients and place in the patient file medical record information such as blood type, known drug allergies, drugs patient is currently taking, dietary restrictions, etc. This data provides a caregiver with information regarding potential adverse reactions a particular patient may experience upon administration of fluids to be administered. In an in-hospital setting this patient-specific information typically is entered or resides in an Admission, Discharge and Transfer (ADT) system or other clinical documentation system. Clinical guidelines and best practices also support a host of non-patient-specific medical information that can be routinely taken into consideration by prescribers of IV medications/fluids such that administering clinicians can avoid inducing patient adverse events. This information can include, but is not limited to drug-drug interactions, blood type matching, appropriate drug dosing limits, impact of current vital signs on treatments, metabolic factors and/or lab results.

Fluids can be delivered according to a medical order defined by a prescribing physician. Delivery orders can specify information such as type of fluid, medication dose, frequency of dose, administration route, etc. In an in-hospital setting these orders can typically reside in a Pharmacy Information System (PIS), Blood Bank Information System (BBIS), or Operating Room Information System (ORIS). Safe delivery of medications or other fluids to patients can require clinicians to execute according to the prescribed medical orders, while simultaneously taking into consideration patient-specific health characteristics (e.g. blood type) and history (e.g. medications previously administered, allergies), drug-specific clinical guidelines, and a host of environmental circumstances such as current vital signs, time, etc.

Figure 1:
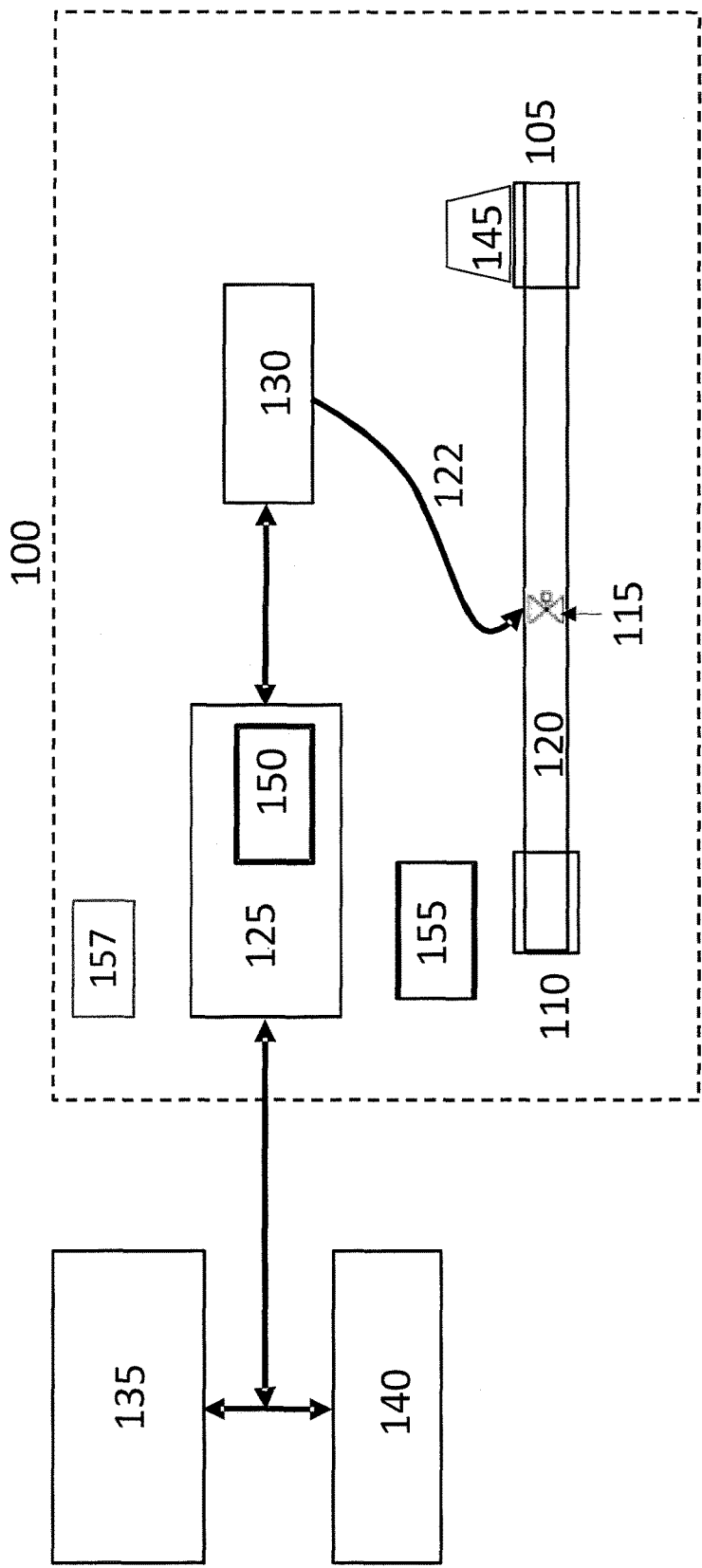
FIG. 1 is a diagram illustrating a system for controlling flow in a fluid delivery pathway.

Turning now to FIG. 1, the system 100 can include a fluid delivery inlet 105 connected to a fluid delivery outlet 110 and one or more programmable flow control valves 115 positioned within the flow path 120 between the inlet 105 and the outlet 110. The system 100 can include a microprocessor 125 that interacts bi-directionally with a configurable rules engine 130. The configurable rules engine 130 can send flow state commands 122 to the flow control valve 115 in the flow path 120. The microprocessor 125 also can communicate with an internal memory 150 and be powered by a power source 155. The system 100 also can include a transmitter/receiver 157.

The microprocessor 125 can communicate with one or more external systems 135. Communication between the system 100 described herein and the one or more external systems 135 can include wired or wireless communication methods. The external system 135 also can include, for example, a data collection system such as a personal computer or computer server running various healthcare information systems such as PIS, BBIS, ORIS, or ADT systems. Additionally, the external system 135 also can be a medical device such as an IV infusion. The system 100 can include a fluid source reader 145 coupled to the inlet 105 and configured to detect one or more information sources carried by the fluid source connected to the inlet 105. Information detected by the fluid source reader 145 can be indicative of a characteristic of the fluid contained within the fluid source container, such as type, volume, concentration, expiration, manufacturer's information regarding contents, etc. The information can be detected by the fluid source reader 145 according to a variety of methods, including but not limited to optical, magnetic, mechanical, conductive, switchable, proximity sensors, IrDA, RFID, etc. Communication systems between inlets, fluid source readers and fluid source identification systems are described in detail in U.S. Pat. Nos. 8,394,053, filed Nov. 6, 2009; 8,355,753, filed Apr. 22, 2010; and 8,385,972, filed Nov. 2, 2010, which are each incorporated by reference herein in their entirety.

The communication between the microprocessor 125 and the one or more external systems 135 can be bi-directional such that the microprocessor 125 can both receive and transmit flow control input data 140. Flow control input data 140 can include, but are not limited to, 1) information about the fluid source such as type of fluid, volume of fluid, concentration of fluid, etc.; 2) constant patient-specific information such as patient identification number, drug allergies, blood type, etc.; 3) variable patient-specific information such as patient vitals, lab results, current disease states and/or clinical diagnoses, drugs previously administered, etc.; 4) medical orders such as drug, dose, route of administration, treatment schedule, etc.; 5) clinical guidelines such as known drug-drug interactions, recommended treatment protocols, etc.; 6) environmental factors such as time of day, date, temperature, etc.; 7) valve status such as currently open (second state) or currently closed (first state); 8) historic patient information such as disease state, clinical diagnosis, dosing history, etc.; and 9) other miscellaneous information such as manual valve override, etc. Communication between the system 100 and the one or more external systems 135 is discussed in more detail below.

The systems described herein are generally small and light-weight systems that can reduce the risk of serious medical errors and deaths by controlling flow through a fluid delivery pathway. It should be appreciated that the systems described herein can be applied to any care environment where fluids are delivered to patients, including hospitals, clinics, outpatient surgery centers, doctor's offices, home health settings, EMS, ambulances, etc.

The system 100 described herein can be enclosed by a small plastic housing such that fluid inlet 105 and outlet 110 are available for external connections. The housing can enclose the fluid pathway 120, one or more flow control valves 115, and a power source 155. The housing can additionally enclose one or more of a microprocessor 125, a memory 150, a transmitter/receiver 157, a rules engine 130, and a fluid source reader 145. The housing can be a low-cost, single-patient use, sterile, disposable assembly. Alternatively, the housing can include most or all of the system components and be reusable and rechargeable. In some implementations, the reusable housing can mate with and attach to a disposable flow path 120 with the flow control valve 115, power source 155 and transmitter/receiver 157. The disposable housing can be packaged sterile and be provided in a protective pouch. Any one or more of the components of the system 100 can be included or excluded from the housing in any number of alternative implementations.

In some implementations, system 100 can be subdivided and have components distributed such that a portion reside within a disposable sub-housing and the remainder reside outside the disposable sub-housing. The disposable sub-housing can include a subset of memory 150 storing characteristics of the components within the disposable sub-housing relevant for proper operation when the disposable and reusable components are combined to form a complete system 100 (e.g. flow path characteristics, number of fluid inlets, number and arrangement of flow control valves, serial number, etc.).

As mentioned above, the system 100 can include a flow control valve 115 positioned within the flow path 120 between the inlet 105 and the outlet 110. The flow control valve 115 can be a programmable valve that can toggle between two states in response to flow state commands 122 from the configurable rules engine 130. The actual configuration of the valve 115 can vary, but generally the valve type is limited to all-on "OPEN" state or an all-off "CLOSED" state. The valve type can vary including, but not limited to, gate valves, globe valves, T valves, butterfly valves, ball valves, check valves, plug valves, pinch valves, diaphragm valves, and the like.

The flow control valve 115 is generally positioned upstream from the fluid outlet 110 and downstream from the fluid inlet 105, but the actual location of the valve 115 relative to other components of the IV set can vary. FIGS. 2A-2G illustrate various locations for the flow control valve 115 to be positioned within an IV administration set flow path 120. The fluid delivery pathway 120 can have a variety of configurations consistent with commonly used IV fluid delivery sets including for example flow path 120 configured as a single flow path extension set (FIG. 2A), a "Y-site" IV set (FIGS. 2B-2D), a multiple-input to single-output IV set (e.g. triple lumen catheter) (FIGS. 2E-2G), and others as are known in the art. The flow control valve 115 can be positioned within a single flow path 120 between an input fluid connector 205a and an output fluid connector 210 (see FIG. 2A). The flow control valve 115 can be positioned within the single flow path 120 downstream of the Y-site with input 205b (see FIG. 2B). The flow control valve 115 can be positioned within the single flow path 120 upstream of the Y-site with input 205b near input 205a (see FIG. 2C). The flow control valve 115 can be positioned within the Y-site near input 205b (see FIG. 2D). The flow control valve 115 can be positioned within a single flow path 120 upstream of output 210 and downstream of multiple-inputs 205a, 205b, 205c, 205d (see FIG. 2E). The flow control valve 115 can be positioned upstream of the single flow path 120 and downstream of one or more of the multiple-inputs 205a, 205b, 205c, 205d (see FIGS. 2F and 2G).

Similarly, the fluid source reader 145 can be positioned on various segments of the flow path 120 depending on the configuration of the components in the set. In some implementations, the fluid source reader 145 can be positioned in an upstream location along the same flow path as the flow control valve 115. In some implementations, the fluid source reader 145 can be positioned along a different portion of the flow path 120 as the flow control valve 115. For example, in a "Y-site" configuration such as shown in FIG. 2B, the flow control valve 115 can be positioned within the single flow path 120 upstream of output 210 and downstream of the Y-site. In this implementation, the fluid source reader 145 can be positioned upstream of the flow control valve 115 in the same flow path 120 or a different flow path upstream of the Y-site. The fluid source reader 145 can also be positioned upstream of the flow control valve 115 in the same flow path 120 downstream of the Y-site.

Figure 3:
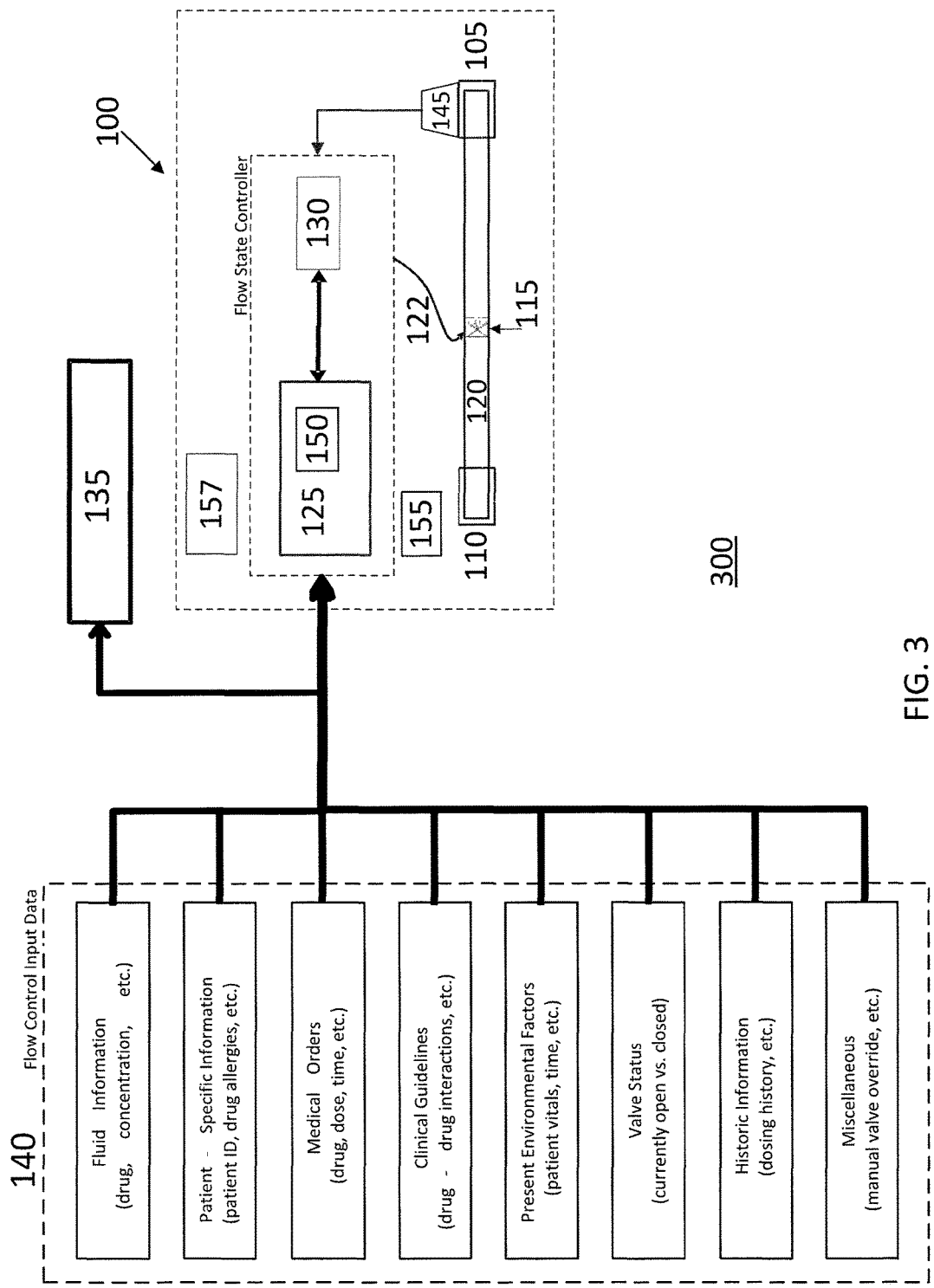
FIG. 3 is a diagram illustrating examples of flow control input data for the system of FIG. 1.

The microprocessor 125 can include a flow control valve software application in combination with rules engine 130 that evaluates combinations of flow control input data 140 against configurable logic for determining the proper state of the flow control valve 115 at any given time prior to or during a treatment regimen or fluid delivery protocol (see the diagram 300 of FIG. 3). Microprocessor 125, rules engine 130 and any associated flow control valve software application and/or configurable rules used by the rules engine 130 can sometimes be collectively referred to as a "flow state controller". Access to the relevant flow control input data 140 allows the system 100 to support, guide, dictate, or perform clinical decisions as to whether or not a particular fluid coupled to the system 100 should be allowed to flow through the flow path 120 to a patient. As described above, the flow control input data 140 can be any data, whether patient-specific or non-patient-specific. The data 140 can be stored in a medical information system, medical database, manually entered, input from an external device and/or system (e.g. vital signs monitor, laboratory information system, temperature sensor, etc.) or based on feedback from the system 100. The data 140 can be static or dynamic. Generally, the data 140 are applicable to and can provide support for making decisions on the appropriateness and/or safety of delivering a fluid to a patient.

The system 100 can be configured to operate in different operative modes. In some implementations, the system 100 operates in a normally CLOSED mode where the baseline state of the flow control valve 115 is closed (first state) and the fluid path 120 is opened during a fluid delivery and then closed again upon completion of the delivery (see FIG. 4). The normally CLOSED mode can be advantageous in higher risk scenarios, for example, in instances in which a caregiver is less experienced or has limited clearance for delivery of care, a fluid administration that requires more checks, involves fluid delivery of higher cost treatments, or administration of fluid treatments where mistakes have dire consequences such as infusion of incompatible blood products, or potent or toxic substances (e.g. chemotherapy). The system 100 also can operate in a normally OPEN mode where the baseline state of the flow control valve 115 is open (second state) and closes only when there is an identified potential safety risk (see FIG. 5). The normally OPEN mode can be desirable or advantageous in scenarios such as, for example, instances in which a caregiver is more experienced or desires more manual control over fluid delivery, or the fluid administration and time-frame requires fewer checks. It should be appreciated that the system 100 can include a manual override mechanism such that at any time during a particular fluid administration the clinician can override the system to an OPEN state allowing them to perform a conventional fluid administration as if the system 100 were not in place in the patient fluid line. The override mechanism can be reset manually by the clinician or automatically by the flow state controller based on a timeout or other applicable rule.

Figure 4:
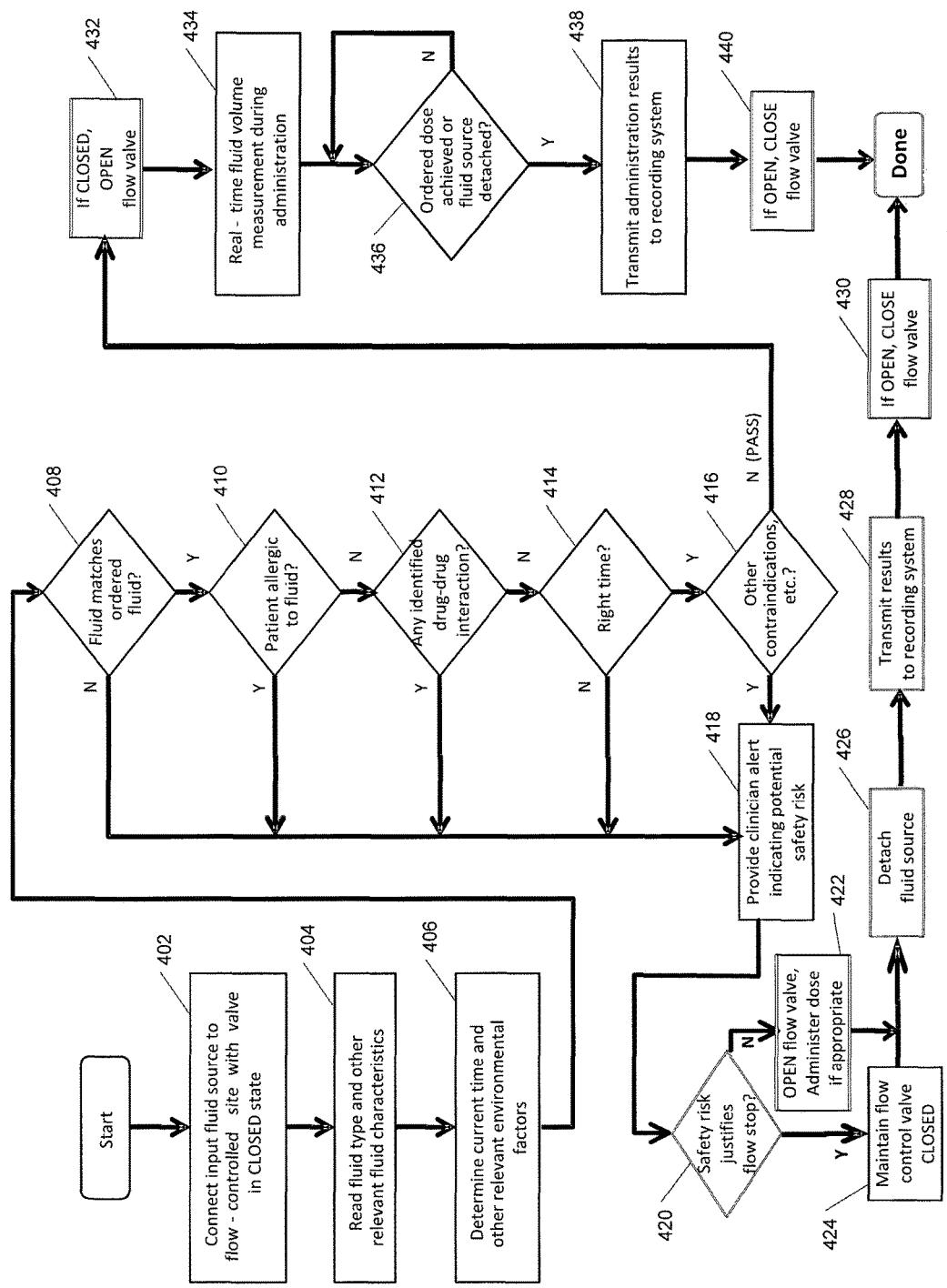
FIG. 4 is a flow chart illustrating an implementation of an operating mode of a system for controlling flow in a fluid delivery pathway.

As shown in the process flow diagram 400 of FIG. 4, the normally CLOSED mode is characterized by the flow control valve 115 normally in a closed state and temporarily opened to allow a fluid to pass through the flow path 120. A fluid source can be connected with fluid inlet 105 while the valve 115 is in a closed state (402). Various relevant characteristics of the fluid source can be identified by the system 100 (404). The current time and other environmental factors can be determined (406). A series of safety checks can be performed by the flow-control software application to assess, for example, whether the fluid coupled to the inlet 105 matches the fluid currently ordered (408), the patient is allergic to the fluid connected to the fluid inlet 105 (410), whether any drug-drug interactions exist (412), whether the current time is the correct time for the administration of the attached fluid (414), or whether any other contraindications to administering the fluid to the patient exist (416). If the system 100 fails one or more of the safety checks, a determination can be made whether the safety risk justifies flow stop (420). If the risk does not justify the flow stop, then the flow valve can be opened and the caregiver can administer the dose (422), otherwise the flow control valve is maintained in a closed position (424) by sending, for example, a flow state command 122 indicating that valve 115 should remain closed. Thereafter, the fluid source can be detached (426), results can be transmitted to a remote system (e.g., a recording system) (428), and if the valve is opened, the valve can be closed (430). In addition, the safety check can trigger an alarm to alert a clinician (418). Data can be transmitted to record the potential safety risk in an external system 135. If the system 100 passes all the safety checks, a flow state command 122 can be sent to the flow control valve 115 to open and allow fluid delivery to the patient.

If the system 100 does not fail one or more of the safety checks, the valve, if closed, can be changed from a closed state to an open state (432). In some implementations, the system 100 can measure fluid volume in real-time during delivery of the fluid (434) and calculate the actual dose delivered and compare it to the ordered dose (436). The ordered "dose" can include a specific fluid volume (e.g. 1 liter of blood) or a quantity calculated by multiplying fluid volume by a fluid source concentration (e.g. 2 mL of 1 mg/mL concentration of morphine fluid source). Once the ordered dose is reached or the system 100 detects the fluid source is detached from the system 100, a flow state command 122 can be sent to close flow control valve 115 (440) in preparation for the next fluid administration. The administration conditions and results can be communicated to the system memory 150 and/or an external system 135 for recording (438).

In some implementations, the rules engine 130 logic can be defined such that triggering an alarm or alarm message to alert the clinician is an independent event from sending a flow control command 122 to flow control valve 115. Rules logic can generate tiered messages and/or flow state commands 122 using multiple trigger points based on the severity of a potential safety risk. For example, if the physician-ordered dose for a fluid is 100 mL, the rules engine 130 can send an message to the clinician without closing the flow control valve 115 when the dose administered reaches 105 mL of fluid. However, if dose administration continues and the cumulative dose volume reaches 110 mL of fluid, the rules engine can send a second clinician message and a flow state command 122 to close flow control.

Figure 5:
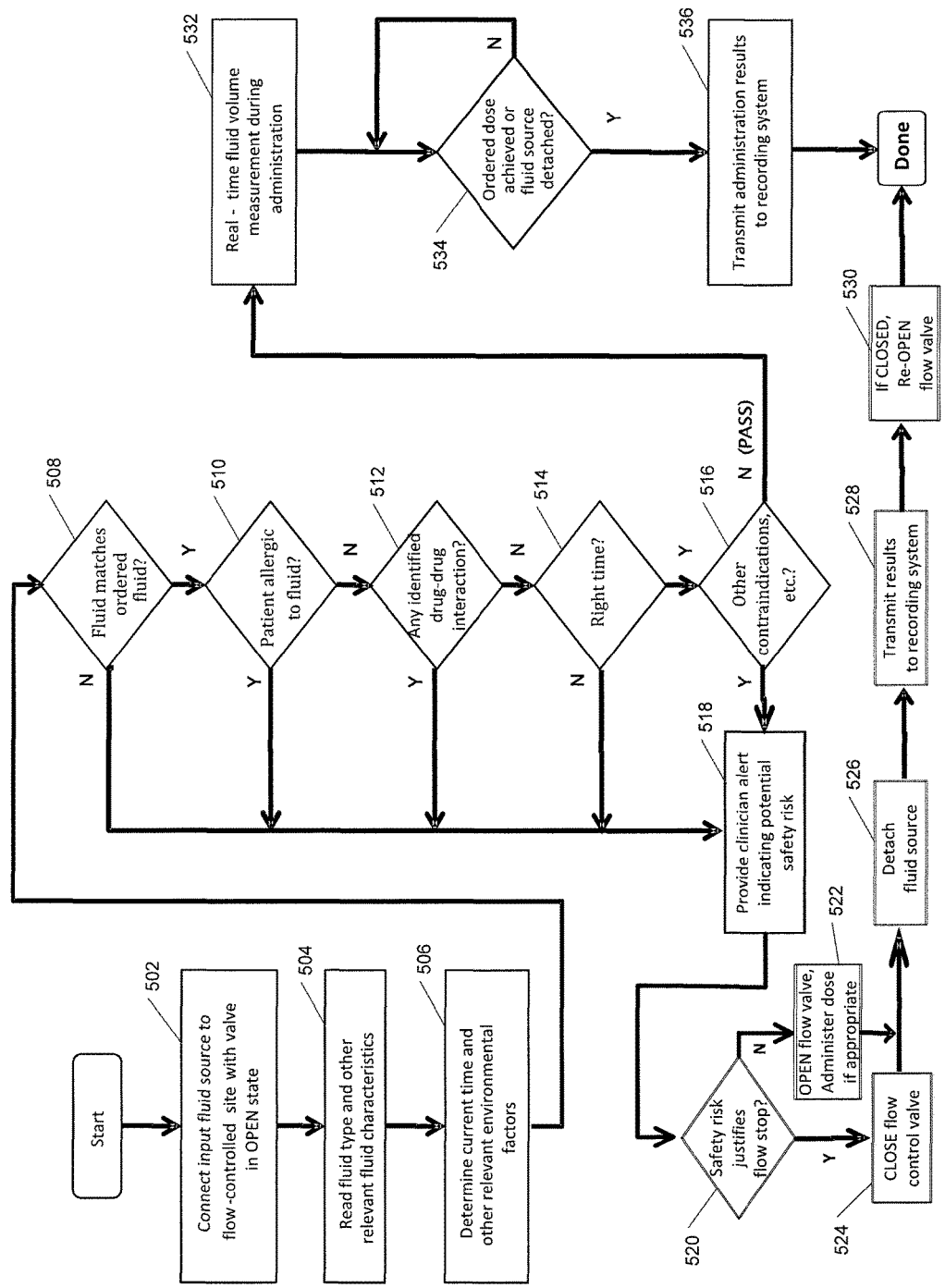
FIG. 5 is a flow chart illustrating another implementation of an operating mode of a system for controlling flow in a fluid delivery pathway.

Referring now to the process flow diagram 500 of FIG. 5, the normally OPEN mode is characterized by the flow control valve 115 normally in an open position to allow fluid to pass through the flow path 120. A fluid source can be connected with a fluid inlet 105 while the flow control valve 115 is in the open state (502). Various relevant characteristics of the fluid source can be identified by the system 100 (504) as well as current time and environmental factors (506). A series of safety checks (508-516) similar to those described in connection with FIG. 4 can be performed by the flow state controller software application (e.g., a rules engine, etc.) using the current flow control input data 140 as described above with respect to FIG. 3. If one or more of the safety checks fail, a flow control command 122 can be sent to close the flow control valve 115. In particular, if one or of the safety checks fail, an alert can be provided (518). Thereafter, it can be determined if the safety risk justifies flow stop (520). If the answer is yes—then the flow control valve can be switched to a closed position (524) and the fluid source detached (526), otherwise the fluid can be administered (522). Results can be transmitted to a recording system (either internal or external) (528) and the valve, if in the closed position, can be switched to an open position (530).

If no safety checks are triggered, fluid volume can be measured in real-time during administration (532). If it is determined during administration that the ordered dose was achieved or the fluid source was detached (534), then proceed to 536, if not the process 534 continues. Once such a determination is made administration results are transmitted to a recording system (internal or external) (536).

As described above, the rules engine can also trigger messages independent of flow state command 122 and transmit the data to record the condition in a memory 150 of the system 100 and/or one or more external systems 135. The valve 115 can re-open after the error condition is resolved, after a clinician manually overrides the flow control valve 115, or once the fluid source is detached. If all the safety checks are passed, a flow state command 122 can be sent to flow control valve 115 to remain open and allow fluid delivery to the patient.

It should be appreciated that the systems described herein can, but need not transmit data to an external system 135 for recording and logging data. For example, the system 100 can incorporate the intelligent flow control features of the programmable flow control valve 115 and provide user feedback (such as alarms and other alert messages) without transmitting, and/or recording the data to an external system 135.

The system 100 can be programmed with information downloaded into the system memory 150 prior to use, in real-time using on-demand connectivity with the external systems 135 or a combination of the two. In some implementations, the system 100 can be pre-programmed according to a subset of static flow control data 140 (e.g. patient blood type, known drug allergies, dose limits, etc.) prior to or upon connection to a patient's fluid line. The system can be programmed using a dockable cradle, wireless communications interface or a wired connector. In some implementations, a low-cost, non-wireless version of the system 100 can be pre-programmed with only non-patient-specific rules such as drug-drug interactions, hard dosing limits, etc. for generic use with any patient. The system 100 can be provided to a buyer including the pre-programmed non-patient-specific information or according to published clinical guidelines and standards. The non-patient-specific information can be programmed prior to clinical use by a manufacturer, care provider or by a hospital pharmacist, or other care setting based on provider-specific rules and operating procedures.

In some implementations, the system 100 can be programmed and/or communicate information in real-time to the one or more external systems 135 using a wireless transmission 157. A variety of wireless transmission hardware and protocols can be used such as RF, IrDA (infrared), Bluetooth, Zigbee, Continue, Wireless USB, Wibree, IEEE 802 relevant standards (e.g., 802.11, 802.15, or 802.16, etc.), Direct Sequence Spread Spectrum; Frequency Hopping Spread Spectrum; cellular/wireless/cordless telecommunication protocols, wireless home network communication protocols, paging network protocols, magnetic induction, satellite data communication protocols, wireless hospital or health care facility network protocols, and other methods. The data transmissions can, in some implementations, be encrypted in order to ensure patient privacy and/or to comply with various laws relating to handling of medical data. The transmitter can have such encryption capabilities or one or more additional chipsets can be incorporated within a region of the system 100 to provide such encryption.

In some implementations, the configurable rules engine 130 can run on a microprocessor 125 remote to the system 100. The commands 122 can be sent to the system 100 in a wireless or wired manner to the flow control valve 115 embedded within the system 100 instructing the flow control valve 115 to open or close.

The system 100 described herein can include one or more mechanisms configured for receiving input from a user to control operation of the system 100 and/or providing feedback to a user from the system 100. For example, the system 100 can incorporate one or more user inputs such as one or more keys, buttons, switches, dials, or touch-screens. The system 100 can incorporate one or more user feedback mechanisms such as one or more LEDs, graphical displays, sounds, speech synthesis technology or vibration mechanisms. The visual, tactile or auditory feedback can include a sequence of notifications such as volume, color, number, intensity, or other feature of the particular feedback mechanism is varied to indicate a particular state of the system 100. In some implementations, one or more of the user inputs and/or feedback mechanisms can be remote to the system 100, such as on a computing device in communication with the system 100 such as by a wired or wireless connection using the transmitter/receiver 157.

The power source 155 can include self-contained power source such as a battery, single-use or rechargeable battery, battery array or other type of power source known in the art. Where the battery is rechargeable, there can be a connector or other interface for attaching the device to an electrical outlet, docking station, portable recharger, or so forth to recharge the battery.

In some implementations, the system 100 can include an internal fluid composition sensor configured to allow the fluid composition and concentration from the fluid source to be empirically determined. The sensor can be positioned downstream of the fluid inlet 105 and upstream of control valve 115. The internal fluid composition sensor can be the sole source of fluid type detection. In some implementations, the composition sensor can be a supplement to fluid source information carried by the fluid source container and detected by a fluid source reader 145.

The system 100 can accommodate a variety of volumes and doses, including fractional doses, or multiple fluid source connections to fulfill the desired treatment protocol of a single patient medical order. For example, a physician can order a 2 mg dose of morphine for a patient. The nurse can connect one 4 mg syringe of morphine, intending to deliver half the syringe to the patient and discard the other half. In this example, the system 100 can alert the clinician that a 4 mg syringe is connected to the system 100 and the potential dose to be delivered to the patient is too high. The system 100 can also prevent overdose by sending a flow state command 122 to close the flow control valve 115 after the first 2 mg of morphine have been delivered to the patient to prevent delivery of remaining 2 mg of morphine. Alternatively, a physician can order 2 mg of morphine for a patient. The care provider can fulfill the order by first connecting a 1 mg syringe of morphine to the system 100 and delivering the full contents of the syringe to the patient and then connecting a second 1 mg syringe of morphine to the system 100 and delivering the full contents of the second syringe to the patient. In either scenario, the physician order for 2 mg have been fulfilled and the system 100 would not provide an alert or constrain fluid flow unless a further morphine syringe is coupled to the system 100.

It should be appreciated that use of the term "therapies" or "fluids" herein is not limited to a specific fluid type, therapy or medication and can include a variety of appropriate fluids. Fluids as used herein can include, but are not limited to medications, blood-based products, nutritional solutions, electrolytes, buffer solutions, lactated Ringer's solutions, sodium bicarbonate, crystalloids, colloids, saline solutions. Blood-based products can include, but are not limited to, any component of the blood for use in blood transfusions, whole blood, fresh frozen plasma, cryoprecipitate, blood substitutes, artificial blood, oxygen-carrying substitutes. Medications can include any therapeutic fluid that can be administered intravenously or another appropriate parenteral route of administration such as intra-arterial, intraosseous, intracerebral, intracardiac, subcutaneous, or intraperitoneal. Similarly, the systems described herein can use any sort of manually administered fluid source and are not limited to a specific IV fluid source type and can include syringes, IV bags, disposable medication cartridges or pouches, IV tubing, etc. It should be appreciated that the systems described herein can be used for delivery of fluids by a variety of routes of administrations. Unless otherwise specified the terms injection, administration, or delivery as they relate to introducing a fluid to a patient is not intended to be limiting to a particular route of manual administration (i.e., administration effected by a human being as opposed to a pump).

The subject matter described herein may be embodied in systems, apparatus, methods, and/or articles depending on the desired configuration. In particular, aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any tangible/non-transitory computer program product, apparatus and/or device (e.g., magnetic discs, optical disks, memory, Programmable Logic Devices (PLDs)) used to provide machine instructions and/or data to a programmable processor.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein (e.g., FIGS. 4, 5 and accompanying text, etc.) do not require the particular order shown, or sequential order, to achieve desirable results. Other embodiments can be within the scope of the claim.

What is claimed is:

1. An apparatus comprising:
a fluid inlet configured to couple to an outlet of a manually administrable fluid source having fluid source information encoded thereon;
a fluid outlet configured to deliver fluid from the manually administrable fluid source to a fluid line leading to a patient;
a fluid flow stop disposed between the fluid inlet and the fluid outlet that prevents fluid flow in a first state and permits fluid flow in a second state;
an identification sensor to detect the fluid source information when the manually administrable fluid source is being coupled or is coupled to the fluid inlet;
a fluid flow sensor disposed between the fluid inlet and the fluid outlet for measuring a specific value of how much fluid has been delivered from the manually administrable fluid source into the fluid inlet;
a flow state controller to selectively cause the fluid flow stop to transition between the first state and the second state automatically in response to the fluid source information being detected by the identification sensor, wherein the flow state controller causes the fluid flow stop to transition from the second state to the first state when a predetermined volume of fluid has been delivered as measured by the fluid flow sensor;
a housing including a reusable sub-housing and a disposable sub-housing, the disposable sub-housing enveloping at least a portion of each of the fluid inlet, the fluid outlet, and the fluid flow stop, wherein the fluid inlet and the fluid outlet are configured relative to the disposable sub-housing such that they are available for external connections, wherein the disposable sub-housing is operatively coupled to the reusable sub-housing, wherein the reusable sub-housing is intended for use by a plurality of patients and the disposable sub-housing is intended for use by a single patient; and
a memory within the disposable sub-housing storing a characteristic of a fluid flow path between the fluid inlet and the fluid outlet, a number of fluid inlets, a number of flow control valves, and an arrangement of the flow control valves.

2. The apparatus as in claim 1, wherein the flow state controller uses a plurality of rules to determine whether to transition the fluid flow stop between the states.

3. The apparatus as in claim 2, wherein the flow state controller polls at least one remote data source to obtain at least a portion of the rules.

4. The apparatus of claim 2, wherein the flow state controller uses a rules engine that utilizes flow control input data to determine whether to transition the fluid flow stop between the states, wherein the flow control input data is selected from a group consisting of: fluid information, patient-specific information, medical order information, clinical guideline information, environmental factors, flow control valve status, and historical information.

5. The apparatus as in claim 2, wherein the rules are utilized by a rules engine that takes into account the fluid source information and flow control input data selected from a group consisting of: fluid information, patient-specific information, medical order information, clinical guideline information, environmental factors, flow control valve status, and historical information.

6. The apparatus as in claim 5, wherein the flow state controller comprises the rules engine and the rules engine is programmable.

7. The apparatus of claim 5, further comprising: a communications module configured to transmit at least one of the flow control input data, rules engine output data, and data characterizing the manually administrable fluid source to a remote data processing apparatus and receive the at least one of the flow control input data, the rules engine output data, and the data characterizing the manually administrable fluid source from the remote data processing apparatus.

8. The apparatus of claim 5, further comprising: an interface to provide at least one of audio and visual feedback to a user characterizing one or more of the fluid source information, a volume of fluid administration from the manually administrable fluid source, rules engine information, and rules engine output.

9. The apparatus of claim 8, wherein the interface provides an indication to the user when the fluid flow stop is in the first state.

10. The apparatus of claim 8, wherein the interface provides an indication to the user of one or more of the rules used by the rules engine causing a fluid flow stop state transition.

11. The apparatus of claim 8, wherein the interface provides an indication to the user without a fluid flow stop state transition.

12. The apparatus of claim 8, wherein the interface displays medication administration information associated with the fluid.

13. The apparatus of claim 8, wherein the memory stores medication administration information.

14. The apparatus of claim 13, further comprising: a communications module configured to transmit the medication administration information to a remote data source and receive the medication administration information from the remote data source.

15. The apparatus of claim 8, wherein the interface is adjacent to the fluid inlet.

16. The apparatus of claim 8, wherein the interface is remote from the fluid inlet.

17. The apparatus as in claim 1, further comprising: a fluid composition sensor to characterize composition of the fluid when the manually administrable fluid source is coupled to the fluid inlet; and wherein the flow state controller further selectively causes the fluid flow stop to transition between the first state and the second state based on the composition detected by the fluid composition sensor.

18. The apparatus as in claim 1, wherein the flow state controller transmits data characterizing the fluid source information detected by the identification sensor to a remote rules engine that sends a signal indicating whether to change the state of the fluid flow stop.

19. The apparatus of claim 1, wherein the fluid is medication and the fluid source information characterizes one or more of a group consisting of: medication type, medication concentration, medication volume, medication expiration date, a dosage form of the medication, dose instructions for the medication, administration instructions for a specific patient, medication formulation, medication manufacturer information, a re-packager of the medication, a distributor of the medication, medication package form, medication package size, medication package serial number, medication lot number, blood type, an NDC code (National Drug Code), a segment of an NDC code identifying a corresponding medication product, a segment of an NDC code identifying a corresponding medication package, a unique identifier code, a human readable alphanumeric string, and a machine readable code.

20. The apparatus of claim 1, wherein the fluid source information is a code or an identifier used to reference a secondary data set that is characteristic of the fluid contained in the manually administrable fluid source.

21. The apparatus of claim 20, wherein the memory stores the secondary data set.

22. The apparatus of claim 20, further comprising: a remote data store coupled to the flow state controller by at least one network storing the secondary data set.

23. The apparatus of claim 22, wherein the remote data store forms part of at least one of a medical device and a medical information system.

24. The apparatus of claim 1, wherein the transition between the states is automatically initiated and executed by the flow state controller without user intervention.

25. The apparatus of claim 1, wherein the transition between the states is automatically initiated and executed by the flow state controller as a result of coupling the outlet of the manually administrable fluid source to the fluid inlet.

26. The apparatus of claim 1, further comprising: a manual override element which, when activated by a user, causes the flow state controller to cause the fluid flow stop to transition from the first state to the second state.

27. The apparatus of claim 1, further comprising at least one additional fluid inlet, wherein each additional fluid inlet is configured to couple to an outlet of at least one additional manually administrable fluid source, wherein each additional manually administrable fluid source has fluid source information thereon.

28. The apparatus of claim 27, further comprising at least one additional fluid flow stop, wherein each additional fluid flow stop is coupled to the flow state controller to selectively prevent fluid flow in a respective one of the additional fluid inlets.

29. The apparatus of claim 1, wherein the fluid flow stop is maintained in the first state until it is determined, by using the fluid source information, to transition the fluid flow stop to the second state.

30. The apparatus of claim 1, wherein the fluid flow stop is maintained in the second state until it is determined, by using the fluid source information, to transition the fluid flow stop to the first state.

31. The apparatus of claim 1, wherein the flow state controller receives data characterizing the patient that is used, in combination with the fluid source information, to determine whether to transition the fluid flow stop between the states.

32. The apparatus of claim 31, wherein the data characterizing the patient comprises at least one medication order, the at least one medication order being used to confirm whether the fluid in the manually administrable fluid source matches one or more parameters specified by the at least one medication order.

33. The apparatus of claim 31, wherein the data characterizing the patient comprises a patient identifier and the flow state controller polls at least one remote data store using the patient identifier to obtain reference information for a rules engine to determine whether to transition the fluid flow stop between the states.

34. The apparatus of claim 1, further comprising: an interface providing at least one of audio and visual feedback indicating how much fluid has been delivered as measured by the fluid flow sensor.

35. The apparatus of claim 1, wherein the flow state controller causes the fluid flow stop to transition from the second state to the first state when the predetermined volume of fluid has been delivered as measured by the fluid flow sensor, and after a pre-determined span of time, causes the fluid flow stop to transition from the first state to the second state.

36. The apparatus of claim 1, wherein the identification sensor detects the fluid source information using one or more technologies selected from a group consisting of: optical, magnetic, mechanical, conductive, switchable, infrared, switchable RFID, and proximity sensors.

37. An apparatus as in claim 1, wherein the disposable sub-housing is part of a kit including a sterile pouch enveloping the disposable sub-housing.

38. The apparatus as in claim 1, wherein the housing has a shape and a size allowing a user to hold the housing in a first hand while activating the manually administrable fluid source in a second hand.

39. The apparatus of claim 1, further comprising: a self-contained power source within the housing powering the fluid flow stop, the identification sensor, and the flow state controller.

40. The apparatus of claim 39, further comprising the fluid line, wherein the fluid line is an IV fluid line and the housing is suspended on the IV fluid line.

41. The apparatus of claim 1, wherein the manually administrable fluid source is selected from a group consisting of: syringes, IV bags, disposable medication cartridges, disposable medication pouches, and IV tubing.

42. The apparatus of claim 1, wherein the memory within the disposable sub-housing stores rules used by the flow state controller to selectively cause the fluid flow stop to transition between the first state and the second state automatically in response to the fluid source information being detected by the identification sensor.

43. The apparatus of claim 1, further comprising:
a self-contained power source within the disposable sub-housing that powers the fluid flow stop; and
a transmitter/receiver within the disposable sub-housing that wirelessly communicates with one or more external systems.

44. A method of using the apparatus of claim 1, comprising:
determining, by using the detected fluid source information, whether to transition the fluid flow stop from its current state to its other state; and
causing, by the flow state controller, the fluid flow stop to transition to the other state if it is determined that the fluid flow stop should transition to the other state; or
maintaining the fluid flow stop in the current state if it is not determined that the fluid flow stop should transition to the other state.

45. An apparatus comprising:
a fluid inlet configured to couple to an outlet of a manually administrable fluid source having fluid source information encoded thereon;
a fluid outlet configured to deliver fluid from the manually administrable fluid source to a fluid line leading to a patient;
a fluid flow stop disposed between the fluid inlet and the fluid outlet that prevents fluid flow in a first state and permits fluid flow in a second state;
an identification sensor to detect the fluid source information when the manually administrable fluid source is being coupled or is coupled to the fluid inlet;
a memory storing rules;

a fluid flow sensor disposed between the fluid inlet and the fluid outlet for measuring a specific value of how much fluid has been delivered from the manually administrable fluid source into the fluid inlet;

a flow state controller to selectively cause the fluid flow stop to transition between the first state and the second state automatically in response to the rules as applied to the fluid source information being detected by the identification sensor, wherein the flow state controller causes the fluid flow stop to transition from the second state to the first state when a predetermined volume of fluid has been delivered as measured by the fluid flow sensor; and a housing including a reusable sub-housing and a disposable sub-housing, the disposable sub-housing enveloping at least a portion of each of the fluid inlet, the fluid outlet, and the fluid flow stop, wherein the fluid inlet and the fluid outlet are configured relative to the disposable sub-housing such that they are available for external connections, wherein the disposable sub-housing is operatively coupled to the reusable sub-housing, wherein the reusable sub-housing is intended for use by a plurality of patients and the disposable sub-housing is intended for use by a single patient, wherein the memory is included within the disposable sub-housing, and wherein the memory stores a characteristic of a fluid flow path between the fluid inlet and the fluid outlet, a number of fluid inlets, a number of flow control valves, and an arrangement of the flow control valves.

46. An apparatus comprising:

a fluid inlet configured to couple to an outlet of a manually administrable fluid source having fluid source information encoded thereon;

a fluid outlet configured to deliver fluid from the manually administrable fluid source to a fluid line leading to a patient;

a fluid flow stop disposed between the fluid inlet and the fluid outlet that prevents fluid flow in a first state and permits fluid flow in a second state;

an identification sensor to detect the fluid source information when the manually administrable fluid source is being coupled or is coupled to the fluid inlet;

a communications module to transmit data to at least one remote system storing at least one of rules and reference information and receive the at least one of the rules and the reference information from the at least one remote system;

a fluid flow sensor disposed between the fluid inlet and the fluid outlet for measuring a specific value of how much fluid has been delivered from the manually administrable fluid source into the fluid inlet;

a flow state controller to poll, via the communications module, the at least one remote system with the fluid source information, and based on a response from the at least one remote system, selectively cause the fluid flow stop to transition between the first state and the second state automatically in response to the fluid source information being detected by the identification sensor, wherein the flow state controller causes the fluid flow stop to transition from the second state to the first state when a predetermined volume of fluid has been delivered as measured by the fluid flow sensor; and a housing including a reusable sub-housing and a disposable sub-housing, the disposable sub-housing enveloping at least a portion of each of the fluid inlet, the fluid outlet, and the fluid flow stop, wherein the fluid inlet and the fluid outlet are configured relative to the disposable sub-housing such that they are available for external connections, wherein the disposable sub-housing is operatively coupled to the reusable sub-housing, wherein the reusable sub-housing is intended for use by a plurality of patients and the disposable sub-housing is intended for use by a single patient; and a memory within the disposable sub-housing storing a characteristic of a fluid flow path between the fluid inlet and the fluid outlet, a number of fluid inlets, a number of flow control valves, and an arrangement of the flow control valves.

\* \* \* \* \*